(12) United States Patent
Kaza

(10) Patent No.: US 7,140,877 B2
(45) Date of Patent: *Nov. 28, 2006

(54) SYSTEM AND METHOD FOR POSITIONING TEETH

(75) Inventor: Srinivas Kaza, Santa Clara, CA (US)

(73) Assignee: Align Technology, Inc., Santa Clara, CA (US)

( * ) Notice: Subject to any disclaimer, the term of this patent is extended or adjusted under 35 U.S.C. 154(b) by 296 days.

This patent is subject to a terminal disclaimer.

(21) Appl. No.: 10/820,387

(22) Filed: Apr. 7, 2004

(65) Prior Publication Data

US 2004/0191719 A1  Sep. 30, 2004

Related U.S. Application Data

(63) Continuation of application No. 10/044,385, filed on Jan. 10, 2002, now Pat. No. 6,767,208.

(51) Int. Cl.
*A61C 3/00* (2006.01)

(52) U.S. Cl. .......................... 433/24; 433/214

(58) Field of Classification Search .............. 433/24, 433/29, 213, 214; 378/10, 38, 39, 40, 189, 378/191, 208, 209
See application file for complete search history.

(56) References Cited

U.S. PATENT DOCUMENTS

| | | | |
|---|---|---|---|
| 1,831,390 A | 11/1931 | Lindelov | |
| 2,467,432 A | 4/1949 | Kesling | |
| 3,660,900 A | 5/1972 | Andrews | |
| 3,860,803 A | 1/1975 | Levine | |
| 3,916,526 A | 11/1975 | Schudy | |
| 3,922,786 A | 12/1975 | Lavin | |
| 3,950,851 A | 4/1976 | Bergersen | |
| 3,983,628 A | 10/1976 | Acevedo | |
| 4,001,938 A | 1/1977 | Cooper | |
| 4,014,096 A | 3/1977 | Dellinger | |
| 4,022,419 A | 5/1977 | Haker | |
| 4,161,065 A | 7/1979 | Gigante | |
| 4,195,046 A | 3/1980 | Kesling | |
| 4,323,779 A * | 4/1982 | Albert | 378/98.6 |
| 4,323,799 A | 4/1982 | King et al. | |
| 4,324,546 A | 4/1982 | Heitlinger et al. | |
| 4,324,547 A | 4/1982 | Arcan et al. | |
| 4,348,178 A | 9/1982 | Kurz | |
| 4,478,580 A | 10/1984 | Barrut | |
| 4,500,294 A | 2/1985 | Lewis | |
| 4,504,225 A | 3/1985 | Yoshii | |
| 4,505,673 A | 3/1985 | Yoshii | |
| 4,575,330 A | 3/1986 | Hull | |
| 4,575,805 A | 3/1986 | Moermann et al. | |

(Continued)

FOREIGN PATENT DOCUMENTS

AU  3031677  5/1979

(Continued)

OTHER PUBLICATIONS

Biostar Operation & Training Manual, Great Lakes Orthodontics, Ltd. 199 Fire Tower Drive, Tonawanda, New York 14150-5890, 20 pp.

(Continued)

*Primary Examiner*—Todd E. Manahan
(74) *Attorney, Agent, or Firm*—Townsend and Townsend and Crew LLP

(57) ABSTRACT

A method to create a digital model of a patient's teeth includes creating an impression of the patient's teeth; and scanning the impression using an X-ray source to generate the digital model.

39 Claims, 7 Drawing Sheets

U.S. PATENT DOCUMENTS

| | | |
|---|---|---|
| 4,591,341 A | 5/1986 | Andrews |
| 4,611,288 A | 9/1986 | Duret et al. |
| 4,656,860 A | 4/1987 | Orthuber et al. |
| 4,663,720 A | 5/1987 | Duret et al. |
| 4,671,769 A | 6/1987 | Gill et al. |
| 4,742,464 A | 5/1988 | Duret et al. |
| 4,755,139 A | 7/1988 | Abbatte et al. |
| 4,763,791 A | 8/1988 | Halverson et al. |
| 4,793,803 A | 12/1988 | Martz |
| 4,798,534 A | 1/1989 | Breads |
| 4,836,778 A | 6/1989 | Baumrind et al. |
| 4,837,732 A | 6/1989 | Brandestini et al. |
| 4,845,747 A * | 7/1989 | Koike et al. ............... 378/208 |
| 4,850,864 A | 7/1989 | Diamond |
| 4,856,991 A | 8/1989 | Breads et al. |
| 4,935,635 A | 6/1990 | O'Hara |
| 4,936,862 A | 6/1990 | Walker et al. |
| 4,937,928 A | 7/1990 | van der Zel |
| 4,941,826 A | 7/1990 | Loran et al. |
| 4,964,770 A | 10/1990 | Steinbichler et al. |
| 4,975,052 A | 12/1990 | Spencer et al. |
| 5,011,405 A | 4/1991 | Lemchen |
| 5,017,133 A | 5/1991 | Miura |
| 5,023,895 A * | 6/1991 | McCroskey et al. ........... 378/4 |
| 5,027,281 A | 6/1991 | Rekow et al. |
| 5,028,232 A | 7/1991 | Snow |
| 5,035,613 A | 7/1991 | Breads et al. |
| 5,055,039 A | 10/1991 | Abbatte et al. |
| 5,059,118 A | 10/1991 | Breads et al. |
| 5,078,600 A | 1/1992 | Austin |
| 5,100,316 A | 3/1992 | Wildman |
| 5,119,408 A * | 6/1992 | Little et al. ............... 378/4 |
| 5,121,333 A | 6/1992 | Riley et al. |
| 5,128,870 A | 7/1992 | Erdman et al. |
| 5,131,843 A | 7/1992 | Hilgers et al. |
| 5,131,844 A | 7/1992 | Marinaccio et al. |
| 5,139,419 A | 8/1992 | Andreiko et al. |
| 5,184,306 A | 2/1993 | Erdman et al. |
| 5,186,623 A | 2/1993 | Breads et al. |
| 5,257,203 A | 10/1993 | Riley et al. |
| 5,273,429 A | 12/1993 | Rekow et al. |
| 5,278,756 A | 1/1994 | Lemchen et al. |
| 5,338,198 A | 8/1994 | Wu et al. |
| 5,340,309 A | 8/1994 | Robertson |
| 5,340,433 A | 8/1994 | Crump |
| 5,342,202 A | 8/1994 | Deshayes |
| 5,368,478 A | 11/1994 | Andreiko et al. |
| 5,382,164 A | 1/1995 | Stern |
| 5,386,292 A | 1/1995 | Massen et al. |
| 5,395,238 A | 3/1995 | Andreiko et al. |
| 5,424,836 A | 6/1995 | Weise et al. |
| 5,431,562 A | 7/1995 | Andreiko et al. |
| 5,434,418 A | 7/1995 | Schick |
| 5,440,496 A | 8/1995 | Andersson et al. |
| 5,447,432 A | 9/1995 | Andreiko et al. |
| 5,452,219 A | 9/1995 | Dehoff et al. |
| 5,454,717 A | 10/1995 | Andreiko et al. |
| 5,456,600 A | 10/1995 | Andreiko et al. |
| 5,474,448 A | 12/1995 | Andreiko et al. |
| 5,518,397 A | 5/1996 | Andreiko et al. |
| 5,533,895 A | 7/1996 | Andreiko et al. |
| 5,542,842 A | 8/1996 | Andreiko et al. |
| 5,549,476 A | 8/1996 | Stern |
| 5,550,891 A | 8/1996 | Burbury et al. |
| 5,587,912 A | 12/1996 | Andersson et al. |
| 5,605,459 A | 2/1997 | Kuroda et al. |
| 5,607,305 A | 3/1997 | Andersson et al. |
| 5,621,648 A | 4/1997 | Crump |
| 5,645,421 A | 7/1997 | Slootsky |
| 5,655,653 A | 8/1997 | Chester |
| 5,683,243 A | 11/1997 | Andreiko et al. |
| 5,725,376 A | 3/1998 | Poirier |
| 5,725,378 A | 3/1998 | Wang |
| 5,733,126 A | 3/1998 | Andersson et al. |
| 5,740,267 A | 4/1998 | Echerer et al. |
| 5,851,115 A | 12/1998 | Carlsson et al. |
| 5,866,058 A | 2/1999 | Batchelder et al. |
| 5,880,961 A | 3/1999 | Crump |
| 5,882,192 A | 3/1999 | Bergersen |
| 5,927,973 A | 7/1999 | Hanebaum et al. |
| 5,957,686 A | 9/1999 | Anthony |
| 5,975,893 A | 11/1999 | Chishti et al. |
| 5,995,583 A * | 11/1999 | Schick et al. ............... 378/38 |
| 6,009,314 A * | 12/1999 | Bjork et al. ............... 455/83 |
| 6,049,743 A | 4/2000 | Baba |
| 6,068,482 A | 5/2000 | Snow |
| 6,091,999 A | 7/2000 | Crump et al. |
| 6,099,314 A | 8/2000 | Kopelman et al. |
| 6,158,888 A | 12/2000 | Walker et al. |
| 6,210,162 B1 | 4/2001 | Chishti et al. |
| 6,217,325 B1 | 4/2001 | Chishti et al. |
| 6,217,334 B1 | 4/2001 | Hultgren |
| 6,217,335 B1 * | 4/2001 | Riitano et al. ............... 433/224 |
| 6,227,850 B1 | 5/2001 | Chishti et al. |
| 6,227,851 B1 | 5/2001 | Chishti et al. |
| 6,299,440 B1 | 10/2001 | Phan et al. |
| 6,309,215 B1 | 10/2001 | Phan et al. |
| 6,318,994 B1 | 11/2001 | Chishti et al. |
| 6,767,208 B1 | 7/2004 | Kaza |
| 2002/0081554 A1 * | 6/2002 | Marshall et al. ............ 433/213 |

FOREIGN PATENT DOCUMENTS

| | | |
|---|---|---|
| AU | 517102 | 7/1981 |
| AU | 5598894 | 6/1994 |
| CA | 1121955 | 4/1982 |
| DE | 2749802 | 5/1978 |
| DE | 69327661 | 7/2000 |
| EP | 0091876 | 10/1983 |
| EP | 0299490 | 1/1989 |
| EP | 0376873 | 7/1990 |
| EP | 0490848 | 6/1992 |
| EP | 0541500 | 5/1993 |
| EP | 0667753 | 8/1995 |
| EP | 0731673 | 9/1996 |
| EP | 0774933 | 5/1997 |
| ES | 463897 | 1/1980 |
| FR | 2369828 | 6/1978 |
| FR | 2652256 | 3/1991 |
| GB | 1550777 | 8/1979 |
| JP | 53-058191 | 5/1978 |
| JP | 04-028359 | 1/1992 |
| JP | 08-508174 | 9/1996 |
| WO | WO 90/08512 | 8/1990 |
| WO | WO 91/03980 | 4/1991 |
| WO | WO 91/04713 | 4/1991 |
| WO | WO 94/10935 | 5/1994 |
| WO | WO 98/15227 | 4/1998 |
| WO | WO 98/32394 | 7/1998 |
| WO | WO 98/44865 | 10/1998 |
| WO | WO 98/58596 | 12/1998 |
| WO | WO 00/74374 | 12/2000 |

OTHER PUBLICATIONS

Graber, T.M., D.D.S., M.S.D., Ph.D., Orthodontics Principles and Practice, 2nd. Ed.,W.B. Saunders Co., 1966.

Kuroda, T., DDS, PhD, et al., Three-dimensional dental cast analyzing system using laser scanning, *American Journal of Orthodontics and Dentofacial Orthopedics*, Oct. 1996, pp. 365-369.

Raintree Essix™ & ARS Materials, Inc., Raintree Essix™ Technical Magazine Table of Contents and Essix™ Applications, http://www.essix.com/magazine/default.html (Aug. 13, 1997) 7 pages.

Rekow, Dianne, M.S.M.E., D.D.S., Computer-aided design and manufacturing in dentistry: A review of the state of the art, *The Journal of Prosthetic Dentistry*, vol. 58, No. 4, Oct. 1987, pp. 512-516.

Doyle, "Digital Dentistry" *Computer Graphics World* (Oct. 2000) pp. 50-52, 54.

Redmond et al., "Clinical Implications of Digital Orthodontics" *Am. J. Orthodont. Dentofacial Orthopedics* (2000) 117(2):240-242.

English translation of Japanese Laid-Open Publication No. 63-11148 to inventor T. Ozukuri (Laid-Open on Jan. 18, 1988) pp. 1-7.

U.S. Appl. No. 60/050,342, filed Jun. 20, 1997, 41 pages total.

Alexander et al., "The DigiGraph Work Station Part 2, Clinical Management," *JCO*, (Jul. 1990), pp. 402-407.

Altschuler et al., "Analysis of 3-D Data for Comparative 3-D Serial Growth Pattern Studies of Oral-Facial Structures," IADR Abstracts, Program and Abstracts of Papers, 57th General Session, IADR Annual Session, Mar. 29, 1979-Apr. 1, 1979, New Orleans Marriot, *J. Dent. Res.*, vol. 58, (Jan. 1979), Special Issue A, p. 221.

Altschuler, "3D Mapping of Maxillo-Facial Prosthesis," *AADR* Abstract #607, (1980), 2 pages total.

Altschuler et al., "Laser Electro-Optic System for Rapid Three-Dimensional (3D) Topographic Mapping of Surfaces," *Optical Engineering*, vol. 20, No. 6, (1981), pp. 953-961.

Altschuler et al., "Measuring Surfaces Space-Coded by a Laser-Projected Dot Matrix," *SPIE Imaging Applications for Automated Industrial Inspection and Assembly*, vol. 182, (1979), pp. 187-191.

American Association for Dental Research, Summary of Activities, Mar. 20-23, 1980, Los Angeles, CA, p. 195.

Andersson et al., "Clinical Results with Titanium Crowns Fabricated with Machine Duplication and Spark Erosion," *Acta Odontol. Scand.*, vol. 47, (1989), pp. 279-286.

Andrews, *The Six Keys to Optimal Occlusion Straight Wire*, Chapter 3, pp. 13-24.

Baumrind et al., "A Stereophotogrammetric System for the Detection of Prosthesis Loosening in Total Hip Arthroplasty," NATO Symposium on Applications of Human Biostereometrics, Jul. 9-13, 1978, *SPI*, 166:112-123.

Baumrind et al., "Mapping the Skull in 3-D," Reprinted from *J. Calif. Dent. Assoc.*, vol. 48, No. 2, (1972 Fall Issue), 11 pages total.

Baumrind, "Integrated Three-Dimensional Craniofacial Mapping: Background, Principles, and Perspectives," *Semin. Orthod.*, 7(4):223-232 (Dec. 2001).

Baumrind, "A System for Craniofacial Mapping Through the Integration of Data from Stereo X-Ray Films and Stereo Photographs," an invited paper submitted to the 1975 American Society of Photogram. Symposium on Close-Range Photogram. Systems, University of Ill., Aug. 26-30, 1975, pp. 142-166.

Begole et al., "A Computer System for the Analysis of Dental Casts," *Angle Orthod.*, 51(3):253-259 (Jul. 1981).

Bernard et al., "Computerized Diagnosis in Orthodontics for Epidemiological Studies: A Progress Report," Paper presented at International Association for Dental Research 66th General Session, Mar. 9-13, 1988, Montreal, Canada. The abstract is published in *J Dental Res. Special Issue*, 67:169.

Bhatia et al., "A Computer-Aided Design for Orthognathic Surgery," *Br. J. Oral Maxillofac Surg.*, vol. 22, (1984), pp. 237-253.

Biggerstaff et al., "Computerized Analysis of Occlusion in the Postcanine Dentition," *Am. J. Orthod.*, vol. 61, No. 3, (Mar. 1972), pp. 245-254.

Biostar, Biostar Operation & Training Manual, Great Lakes Orthodontics Ltd., Tonawanda, NY, 20 pages.

Biggerstaff, "Computerized Diagnostic Setups and Simulations," *Angle Orthod.*, vol. 40, No. 1, (Jan. 1970), pp. 28-36.

Boyd et al., "Three-Dimensional Diagnosis and Orthodontic Treatment of Complex Malocclusions with the Invisalign Appliance," *Seminars in Orthodontics*, vol. 7, No. 4 (Dec. 2001), pp. 274-293.

Brandestini et al., "Computer Machined Ceramic Inlays: In Vitro Marginal Adaptation," *J. Dent. Res.*, vol. 64/Special Issue/Abstracts, IADR/AADR Abstracts, (1985), p. 208.

Brook et al., "An Image Analysis System for the Determination of Tooth Dimensions from Study Casts: Comparison with Manual Measurements of Mesio-distal Diameter," *J. Dent. Res.*, vol. 65, No. 3, (Mar. 1986), pp. 428-431.

Burstone (interview), "Dr. Charles J. Burstone on The Uses of the Computer in Orthodontic Practice (Part 1)," *J. Clin. Orthod.*, 13(7):442-53 (Jul. 1979).

Burstone (interview), "Dr. Charles J. Burstone on The Uses of the Computer in Orthodontic Practice (Part 2)," *J. Clin. Orthod.*, 13(8):539-51 (Aug. 1979).

Burstone et al., "Precision Adjustment of the Transpalatal Lingual Arch: Computer Arch Form Predetermination," *Am. J. Orthod.*, vol. 79, No. 2 (Feb. 1981), pp. 115-133.

Cardinal Industrial Finishes, Powder Coatings Information posted at http://www.cardinalpaint.com on Aug. 25, 2000, 2 pages total.

Carnaghan et al., "An Alternative to Holograms for the Portrayal of Human Teeth," *Fourth International Conference Holographic Systems, Components and Applications*, Sep. 13-15, 1993, Issue 379, pp. 228-231.

Chaconas et al., "DigiGraph Work Station, Part 1, Basic Concepts," *JCO*, (Jun. 1990), pp. 360-367.

Chafetz et al., "Subsidence of the Femoral Prosthesis, A Stereophotogrammetric Evaluation," *Clin. Orthop. Relat. Res.*, No. 201, (Dec. 1985), pp. 60-67.

Chiappone, "Constructing the Gnathologic Setup and Positioner," *J. Clin. Orthod.*, vol. 14, pp. 121-133 (1980).

Cottingham, Gnathologic Clear Plastic Positioner, *Am. J. Orthod.*, vol. 55, pp. 23-31 (Jan. 1969).

Crawford, "CAD/CAM in the Dental Office: Does It Work?" *J. Can. Dent Assoc.*, vol. 57, No. 2, (Feb. 1991), pp. 121-123.

Crawford, "Computers in Dentistry: Part 1—CAD/CAM: The Computer Moves Chairside; Part 2—Computers in dentistry. Part two. Francois Duret—a man with vision; Part 3—The computer gives new vision—literally; Part. 4—Bytes 'N Bites: The Computer Moves From The Front Desk To The Operatory," *J. Can. Dent. Assoc.*, (Sep. 1988), 54(9):661-666.

Crooks, "CAD/CAM Comes to USC," *USC Dentistry*, (Spring 1990), pp. 14-17.

Cureton, "Correcting Malaligned Mandibular Incisors with Removable Retainers," *J. Clin. Orthod.*, vol. 30, No. 7, (1996), pp. 390-395.

Curry et al., "Integrated Three-Dimensional Craniofacial Mapping at the Craniofacial Research Instrumentation Laboratory/University of the Pacific," *Semin. Orthod.*, vol. 7, No. 4, (Dec. 2001), pp. 258-265.

Cutting et al., "Three-Dimensional Computer-Assisted Design of Craniofacial Surgical Procedures: Optimization and Interaction with Cephalometric and CT-Based Models," *Plast. Reconstr. Surg.*, vol. 77, No. 6, (Jun. 1986), pp. 877-885.

DCS Dental AG, "The CAD/CAM 'DCS Titan System' for Production of Crowns/Bridges," DSC Production AG, (Jan. 1992), pp. 1-7.

Defranco et al., "Three-Dimensional Large Displacement Analysis of Orthodontic Appliances," *J. Biomech.*, vol. 9, (1976), pp. 793-801.

Dental Institute University of Zurich Switzerland, "Program for International Symposium on Computer Restorations: State of the Art of the CEREC-Method," (May 1991), 2 pages total.

Dentrac Corporation, Dentrac document, pp. 4-13.

DENT-X posted at http://www.dent-x.com/DentSim.htm Sep. 24, 1998, 6 pages total.

Doyle, A., "Digital Dentistry," *Computer Graphics World*, <<www.cgw.com>>, 4 pages (Oct. 2000).

Duret et al., "CAD/CAM Imaging in Dentistry," *Curr. Opin. Dent.*, vol. 1, (1991), pp. 150-154.

Duret et al., "CAD-CAM in Dentistry," *J. Am. Dental Assoc.*, vol. 117, (Nov. 1988), pp. 715-720.

Duret, "The Dental CAD/CAM, General Description of the Project," *Hennson International Product Brochure*, (Jan. 1986), 18 pages total.

Duret, "Vers Une Prosthese Informatisee," (English translation also attached), *Tonus*, vol. 75, (Nov. 15, 1985), pp. 55-57.

Economides, "The Microcomputer in the Orthodontic Office," *JCO*, (Nov. 1979), pp. 767-772.

Elsasser, "Some Observations on the History and Uses of the Kesling Positioner," *Am. J. Orthod.*, (1950), 36:368-374.

Faber et al., "Computerized interactive orthodontic treatment planning," *Am. J. Orthod.*, vol. 73, No. 1, (Jan. 1978), pp. 3646.

Felton et al., "A Computerized Analysis of the Shape and Stability of Mandibular Arch Form," *Am. J. Orthod. Dentofacial. Orthop.*, vol. 92, No. 6, (Dec. 1987), pp. 478-483.

Friede et al., "Accuracy of Cephalometric Prediction in Orthognathic Surgery, Abstract of Papers," *J. Dent. Res.*, vol. 70, (1987), pp. 754-760.

Fütterling et al., "Automated Finite Element Modeling of a Human Mandible with Dental Implants," *WSCG '98—Conference Program*, retrieved from the Internet: <<http://wscg.zcu.cz/wscg98/papers98/Strasser_98.pdf.>>, 8 pages total.

Gao et al., "3-D Element Generation for Multi-Connected Complex Dental and Mandibular Structure," *Proceedings. International Workshop on Medical Imaging and Augmented Reality*, 2001.

Gim-Alldent, Deutschland, Das DUX System: Die Technik, 2 pages total.

Gottleib et al., "JCO Interviews Dr. James A. McNamara, Jr., on the Frankel Appliance: Part 2: Clinical Management," *Journal of Clinical Orthodontics*, vol. 16, No. 6, (Jun. 1982) pp. 390-407.

Grayson, "New Methods for Three Dimensional Analysis of Craniofacial Deformity, Symposium: Computerized Facial Imaging in Oral and Maxiiofacial Surgery," *AAOMS*, (Sep. 13, 1990), 3 pages total.

Guess et al., "Computer Treatment Estimates in Orthodontics and Orthognathic Surgery," *JCO*, (Apr. 1989), pp. 262-28.

Heaven et al., "Computer-based Image Analysis of Artificial Root Surface Caries, Abstracts of Papers," *J. Dent. Res.*, vol. 70, (Apr. 17-21, 1991), p. 528.

Hoffman et al., "Role of Cephalometry for Planning of Jaw Orthopedics and Jaw Surgery Procedures," (Article Summary in English, article in German), *Informatbnen*, (Mar. 1991), pp. 375-396.

Hojjatie et al., "Three-Dimensional Finite Element Analysis of Glass-Ceramic Dental Crowns," *J Biomech.* (1990) vol. 23, No. 11, pp. 1157-1166.

Huckins, "CAD-CAM Generated Mandibular Model Prototype from MRI Data," *AAOMS*, (1999), p. 96.

JCO Interviews, "Craig Andreiko, DDS, MS on the Elan and Orthos Systems," *JCO*, (Aug. 1994), pp. 459-468.

JCO Interviews, "Dr. Homer W. Phillips on Computers in Orthodontic Practice," Part 2, *JCO*, (Dec. 1983), pp. 819-831.

Jerrold, "The Problem, Electronic Data Transmission and the Law," *AJO-DO*, (Apr. 1988), pp. 478-479.

Jones et al., "An Assessment of the Fit of a Parabolic Curve to Pre- and Post-Treatment Dental Arches," *Br. J. Orthod.*, vol. 16, (1989), pp. 85-93.

Kamada et al., "Case Reports On Tooth Positioners Using LTV Vinyl Silicone Rubber," J. Nihon University School of Dentistry, (1984), 26(1): 11-29.

Kamada et al., "Construction of Tooth Positioners with LTV Vinyl Silicone Rubber and Some Case Reports," J. Nihon University School of Dentistry, (1982), 24(1):1-27.

Kanazawa et al., "Three-Dimensional Measurements of the Occlusal Surfaces of Upper Molars in a Dutch Population," *J. Dent Res.*, vol. 63, No. 11, (Nov. 1984), pp. 1298-1301.

Kesling et al., "The Philosophy of the Tooth Positioning Appliance," *Am. J. Orthod. Oral Surg.*, (1945), 31:297-304.

Kesling, "Coordinating the Predetermined Pattern and Tooth Positioner with Conventional Treatment," *Am. J. Orthod. Oral Surg.*, (1946), 32:285-293.

Kleeman et al., "The Speed Positioner," *J. Clin. Orthod.*, (1996), 30:673-680.

Kunii et al., "Articulation Simulation for an Intelligent Dental Care System," *Displays* (1994) 15:181-188.

Kuroda et al., "Three-Dimensional Dental Cast Analyzing System Using Laser Scanning," *Am. J. Orthod. Dentofac. Orthop.*, (1996), 110:365-369.

Laurendeau et al., "A Computer-Vision Technique for the Acquisition and Processing of 3-D Profiles of Dental Imprints: An Application in Orthodontics," *IEEE Trans. Med. Imaging*, vol. 10, No. 3, (Sep. 1991), pp. 453-461.

Leinfelder et al., "A New Method for Generating Ceramic Restorations: a CAD-CAM system," *J. Am. Dent. Assoc.*, vol. 118, No. 6, (Jun. 1989), pp. 703-707.

Manetti et al., "Computer-aided cefalometry and new mechanics in orthodontics," *Fortschr. Kieferorthop.*, (Oct. 1983), 44(5):370-376.

McCann, "Inside the ADA,"*J. Am. Dent. Assoc.*, vol. 118,(Mar. 1989), p. 286-294.

McNamara et al., "Invisible Retainers," *J. Clin. Orthod.*, (Aug. 1985), pp. 570-578.

McNamara et al., "Orthodontic and Orthopedic Treatment in the Mixed Dentition," Needham Press, Jan. 1993, pp. 347-353.

Moermann et al., "Computer Machined Adhesive Porcelain Inlays: Margin Adaptation after Fatique Stress," IADR Abstract 339, *J. Dent. Res.*, vol. 66(a), (1987), p. 763.

Mörmann et al., "Marginale Adaptation von adhäsuven Porzellaninlays in vitro," Separatdruck aus: Schweiz. Mschr. Zahnmed. 95: 1118-1129, (1985).

Nahoum, "The Vacuum Formed Dental Contour Appliance," *N. Y. State Dent. J.*, (Nov. 1964), vol. 30, No. 9, pp. 385-390.

Nash, "CEREC CAD/CAM Inlays: Aesthetics and Durability in a Single Appointment," *Dent. Today*, (Oct. 1990), pp. 20, 22-23, 54.

Nishiyama et al., "A New Construction of Tooth Repositioner by LTV Vinyl Silicone Rubber," J. Nihon University School of Dentistry, (1977), 19(2):93-102.

Paul et al., "Digital Documentation of Individual Human Jaw and Tooth Forms for Application in Orthodontics, Oral Surgery and Forensic Medicine," *Industrial Electronics Society, Proceedings of the 24th Annual Conference of the IEEE*, Aug. 31-Sep. 1998, vol. 4, pp. 2415-2418.

Pinkham, "'Foolish' Concept Propels Technology," *Dentist*, (Jan./Feb. 1989), 3 pages total.

Pinkham, "Inventor's CAD/CAM May Transform Dentistry," *Dentist*, (Sep. 1990), 3 pages total.

Ponitz, "Invisible Retainers," *Am J. Orthod.*, vol. 59, No. 3, (Mar. 1971), pp. 266-272.

Procera Research Projects, "Procera Research Projects 1993—Abstract Collection," (1993), pp. 3-28.

Proffit et al., *Contemporary Orthodontics* (Second Ed.) Chapter 15, Mosby Inc, (Oct. 1992 ), pp. 470-533.

Raintree Essix & ARS Materials, Inc., "Raintree Essix, Technical Magazine Table of contents and Essix Appliances," <httpz;// www.essix.com/magazine/default.html>, (Aug. 13, 1997), 7 pages.

Redmond, W., "Clinical Implications of Digital Orthodontics," *Am. J. Orthod. Dentofacial. Orthop.*, 117(2):240-243.

Rekow, "A Review of the Developments in Dental CAD/CAM Systems," (contains references to Japanese efforts and content of the papers of particular interest to the clinician are indicated with a one-line summary of their content in the bibliography), *Curr. Opin. Dent.*, (Jun. 1992), vol. 2, pp. 25-33.

Rekow, "CAD/CAM in Dentistry: A Historical Perspective and View of the Future," *J. Can. Dent. Assoc.*, vol. 58 No. 4, (Apr. 1992), pp. 283, 287-288.

Rekow, "Dental CAD-CAM Systems: What is the State of the Art?" *J. Am. Dent. Assoc.*, vol. 122, (1991), pp. 43-48.

Rekow, "Feasibility of an Automated System for Production of Dental Restorations," PhD Thesis, Univ. of Minnesota, (Nov. 1988), 244 pages total.

Rekow, "CAD/CAM for Dental Restorations—Some of the Curious Challenges," *IEEE Trans. Biomed. Eng.*, 38(4):314-318 (Apr. 1991).

Rekow, "Comparison of Three Data Acquisition Techniques for 3-D Tooth Surface Mapping," *Bioengineering in Dentistry*, Annual International Conference of the IEEE Engineering in Medicine and Biology Society, 13:1:0344-0345 (1991).

Richmond et. al., "The Development of the PAR Index (Peer Assessment Rating): Reliability and Validity," *European Journal of Orthodontics* (1992) 14:125-139.

Richmond et al., "Research Reports; The Development of a 3D Cast Analysis System," *Br. J. Orthod.*, (Jan. 1986), 13(1):53-54.

Richmond, "Recording The Dental Cast In Three Dimensions," *Am. J. Orthod. Dentofac. Orthop.*, vol. 92, No. 3, (Sep. 1987), pp. 199-206.

Rudge, "Dental arch analysis: arch form. A review of the literature," *Eur. J. Orthod.*, vol. 3, No. 4, (1981), pp. 279-284.

Sakuda et al., "Integrated Information-Processing System In Clinical Orthodontics: An Approach with Use of a Computer Network System," *Am. J. Orthod. Dentofac. Orthop.*, vol. 101, No. 3, (Mar. 1992), pp. 210-220.

Schellhas et al., "Three-Dimensional Computed Tomography in Maxillofacial Surgical Planning," *Arch. Otolamgol. Head Neck Surg.*, vol. 114, (Apr. 1988), pp. 438-442.

Schroeder et al., Eds. *The Visual Toolkit, Prentice Hall PTR*, New Jersey (1998) Chapters 6, 8 & 9, (pp. 153-210,309-354, and 355-428, respectively).

Shilliday, "Minimizing finishing problems with the mini-positioner," *Am. J. Orthod.*, (1971), 59:596-599.

Siemens, "CEREC—Computer-Reconstruction, High Tech in der Zahnmedizin," 14 page total.

Sinclair, The Readers' Corner, *Journal of Clinical Orthodontics*, vol. 26, No. 6, (Jun. 1992) pp. 369-372.

Sirona Dental Systems GmbH, *CEREC 3D, Manuel utiiisateur*, Version 2.0X, (in French), (2003), 114 pages total.

Stoll et al., "Computer-aided Technologies in Dentistry," (Article Summary in English, article in German), *Dtsch Zahna'rztl, Z* 45, pp. 314-322, (1990).

Tru-Tain Orthodontic & Dental Supplies, Product Brochure, Rochester, Minnesota 55902, 16 pages total.

U.S. Department of Commerce, National Technical Information Service, "Automated Crown Replication Using Solid Photography SM," *Solid Photography Inc.*, Melville, NY, (Oct. 1977), 20 pages total.

U.S. Department of Commerce, National Technical Information Service, "Holodontography: An Introduction to Dental Laser Holography," *School of Aerospace Medicine*, Brooks AFB TX, (Mar. 1973), 37 pages total.

Van Der Linden et al., "Three-Dimensional Analysis of Dental Casts by Means of the Optocom," *J. Dent. Res.*, (Jul.-Aug. 1972),51(4):1100.

Van Der Linden, "A New Method to Determine Tooth Positions and Dental Arch Dimensions," *J. Dent. Res.*, (Jul.-Aug. 1972), vol. 51, No. 4, p. 1104.

Van Der Zel, "Ceramic-Fused-To-Metal Restorations with a New CAD/CAM System," *Quintessence Int.*, vol. 24, No. 11, (1993), pp. 769-778.

Varady et al., "Reverse Engineering Of Geometric Models—An Introduction," *Computer-Aided Design*, 29 (4):255-268, (1997).

Verstreken et al., "An Image-Guided Planning System for Endosseous Oral Implants," *IEEE Transactions on Medical Imagining*, vol. 17, No. 5, (Oct. 1998), pp. 842-852.

Warunek et al., "Clinical Use of Silicone Elastomer Applicances," *JCO*, (1989), XXIII(10):694-700.

Warunek et al., "Physical and Mechanical Properties of Elastomers in Orthodonic Positioners," *Am. J. Orthod. Dentofac. Orthop*, vol. 95, No. 5, (May 1989), pp. 399-400.

Wells, "Application of the Positioner Appliance in Orthodontic Treatment," *Am. J. Orthodont.*, (1970), 58:351-366.

Williams, "Dentistry and CAD/CAM: Another French Revolution," *J. Dent. Pract. Adm.*, (Jan./Mar. 1987), pp. 2-5.

Williams, "The Switzerland and Minnesota Developments in CAD/CAM," *J. Dent. Pract. Adm.*, (Apr./Jun. 1987), pp. 50-55.

Wishan, "New Advances in Personal Computer Applications for Cephalometric Analysis, Growth Prediction, Surgical Treatment Planning and Imaging Processing," Symposium: Computerized Facial Imaging in Oral and Maxillofacial Surgery Presented on Sep. 13, (Aug. 1990), *J. Oral Maxillofacial Surg.*, 48(8):5.

Yamamoto et al., "Optical Measurement of Dental Cast Profile and Application to Analysis of Three-Dimensional Tooth Movement in Orthodontics," *Frontiers Med. Biol. Engng.*, vol. 1, No. 2, (1988), pp. 119-130.

Yamamoto et al., "Three-Dimensional Measurement of Dental Cast Profiles and Its Applications to Orthodontics," *Annual Int'l Conf. of IEEE Engineering in Medicine and Biology Society*, vol. 12, No. 5, (1990), pp. 2051-2053.

Yamany et al., "A System for Human Jaw Modeling Using Intra-Oral Images, A System for Human Jaw Modeling Using Intra-Oral Images," *In IEEE-EMBS*, vol. 2, (Oct. 29-Nov. 1998) pp. 563-566, 1998.

Yoshii, "Research on a New Orthodontic Appliance: The Dynamic Positioner (D.P.)—1. The D.P. concept and implementation of Transparent Silicone Resin (Orthocon)," *Nippon Dental Review*, vol. 452, Jun. 1980, pp. 61-74.

Yoshii, "Research on A New Orthodontic Appliance: The Dynamic Positioner (D.P.)—II. Th D.P. Manufacturing Procedure and Clinical Applications," *Nippon Dental Review*, vol. 454, Aug. 1980, pp. 107-130.

Yoshii, "Research on a New Orthodontic Appliance: The Dynamic Positioner (D.P.)—III. The General Concept of the D.P. Method and its Therapeutic Effect, Part 1, Dental and Functional Reversed Occlusion Case Reports," *Nippon Dental Review*, vol. 457, Nov. 1980, pp. 146-164.

Yoshii, "Research on a New Orthodontic Appliance: The Dynamic Positioner (D.P.)—III. The General Concept of the D.P. Method and its Therapeutic Effect, Part 2. Skeletal reversed Occlusion Case Reports," *Nippon Dental Review*, vol. 458, Dec. 1980, pp. 112-129.

\* cited by examiner

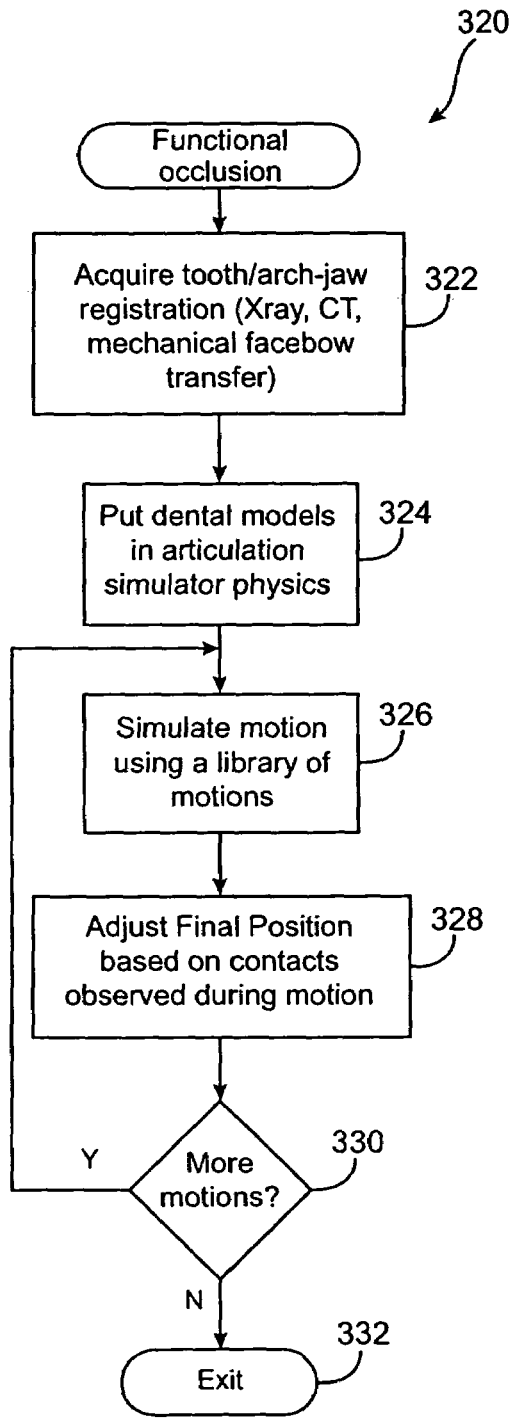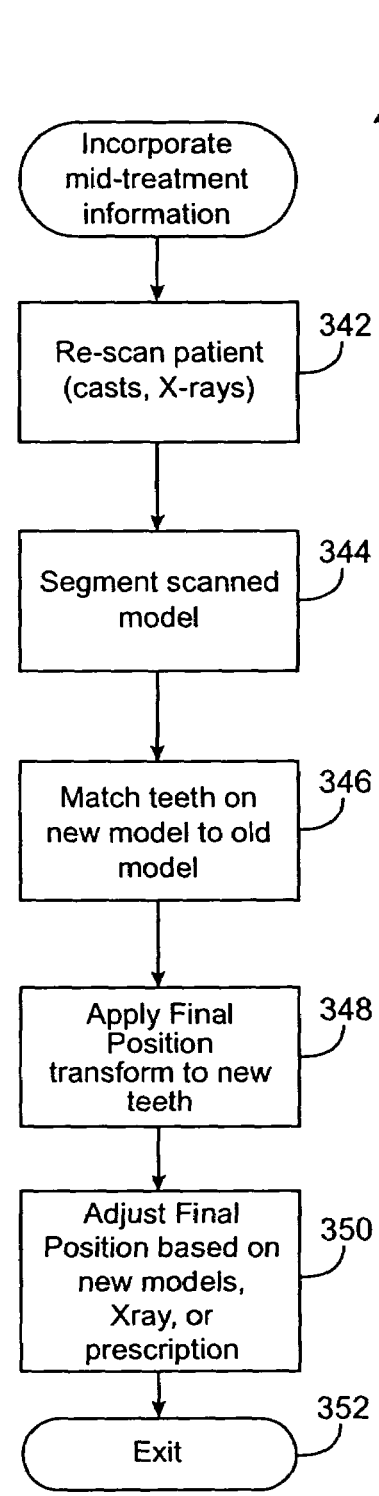
FIG. 5
FIG. 6

SYSTEM AND METHOD FOR POSITIONING TEETH

CROSS-REFERENCES TO RELATED APPLICATIONS

The present application is a continuation of U.S. patent application Ser. No. 10/044,385, filed Jan. 10, 2002 now U.S. Pat. No. 6,767,208, the full disclosure of which is incorporated herein by reference.

BACKGROUND OF THE INVENTION

The present invention is related generally to the field of orthodontics, and more particularly to a system and a method for gradually repositioning teeth.

BRIEF SUMMARY OF THE INVENTION

A fundamental objective in orthodontics is to realign a patient's teeth to positions where the teeth function optimally and aesthetically. Typically, appliances such as braces are applied to the teeth of the patient by a treating orthodontist. Each appliance exerts continual forces on the teeth which gradually urge the teeth toward their ideal positions. Over a period of time, the orthodontist adjusts the appliances to move the teeth toward their final destination.

The process of attaching the braces to teeth is tedious and painful. Additionally, each visit to the orthodontist is time consuming and expensive. The process is further complicated by uncertainties in determining a final arrangement for each tooth. Generally, the final tooth arrangement is determined by the treating orthodontist who writes a prescription. Traditionally, the prescription is based on the orthodontist's knowledge and expertise in selecting the intended final position of each tooth and without a precise calculation of forces being exerted on the teeth when they contact each other.

A method to create a digital model of a patient's teeth includes creating an impression of the patient's teeth; and scanning the impression using an X-ray source to generate the digital model.

Advantages of the invention include one or more of the following. The system eliminates the need to pour plaster models. The system generates the digital models independent of geometry of teeth since X-rays always pass through. The system assists with the alignment of upper and lower jaws into a bite using the scan model of a bite and allows for accurate bite alignment. Digital detailing allows a cleanup of any defects in the model. The system assists in the reconstruction of teeth in cases where they are distorted/chipped, for example. Bite articulation can be done in a virtual mode. The system can scan impressions as well as plaster models. When a prescription or other final designation is provided, a computer model can be generated and manipulated to match the prescription. The prescription may be automatically interpreted in order to generate an image as well as a digital data set representing the final tooth arrangement.

BRIEF DESCRIPTION OF THE DRAWINGS

FIG. 5 is a flow chart illustrating a process for performing functional occlusion on the patient's teeth.

FIG. 6 is a flow chart illustrating an optional process for incorporating midtreatment information to the final placement of the patient's teeth.

DETAILED DESCRIPTION OF THE INVENTION

Figure 1:
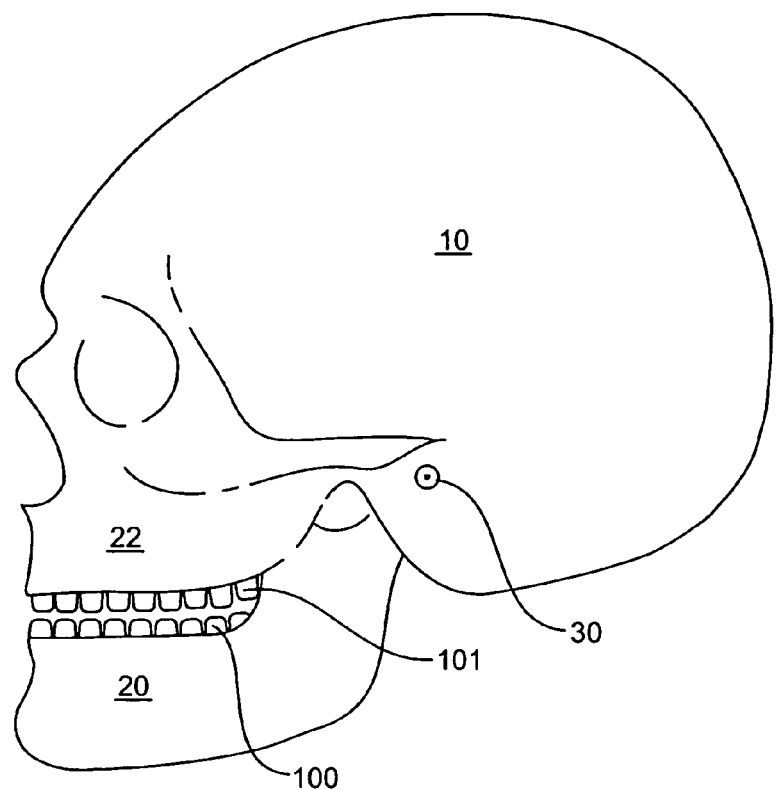
FIG. 1 is an elevational diagram showing the anatomical relationship of the jaws of a patient.

FIG. 1 shows a skull 10 with an upper jaw bone 22 and a lower jaw bone 20. The lower jaw bone 20 hinges at a joint 30 to the skull 10. The joint 30 is called a temporomandibular joint (TMJ). The upper jaw bone 22 is associated with an upper jaw 101, while the lower jaw bone 20 is associated with a lower jaw 100.

A computer model of the jaws 100 and 101 is generated, and a computer simulation models interactions among the teeth on the jaws 100 and 101. The computer simulation allows the system to focus on motions involving contacts between teeth mounted on the jaws. The computer simulation allows the system to render realistic jaw movements which are physically correct when the jaws 100 and 101 contact each other. The model of the jaw places the individual teeth in a treated position. Further, the model can be used to simulate jaw movements including protrusive motions, lateral motions, and "tooth guided" motions where the path of the lower jaw 100 is guided by teeth contacts rather than by anatomical limits of the jaws 100 and 101. Motions are applied to one jaw, but may also be applied to both jaws. Based on the occlusion determination, the final position of the teeth can be ascertained.

Figures 2A, 2B:
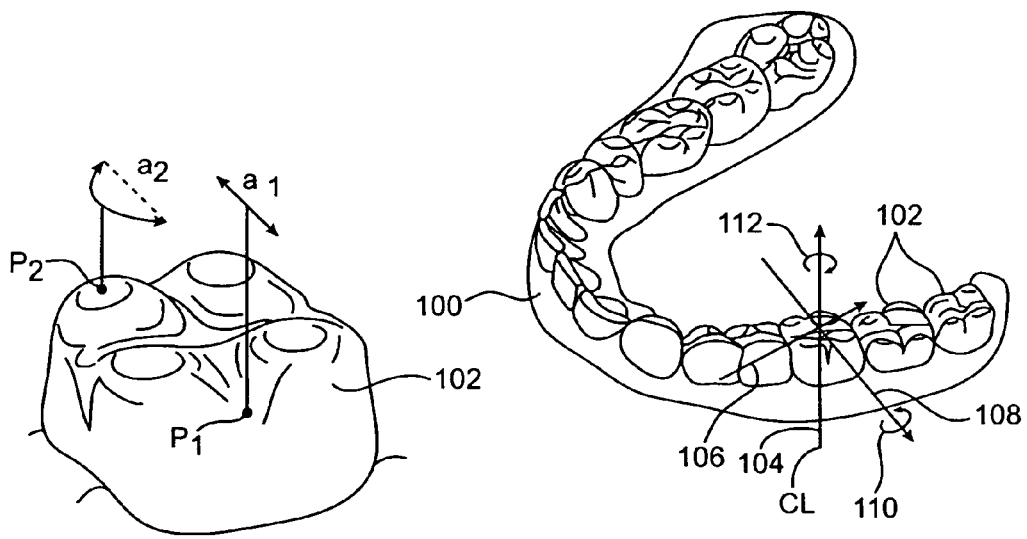
FIG. 2A illustrates in more detail the patient's lower jaw and provides a general indication of how teeth may be moved by the methods and apparatus of the present invention.
FIG. 2B illustrates a single tooth from FIG. 2A and defines how tooth movement distances are determined.

Referring now to FIG. 2A, the lower jaw 100 includes a plurality of teeth 102, for example. At least some of these teeth may be moved from an initial tooth arrangement to a final tooth arrangement. As a frame of reference describing how a tooth may be moved, an arbitrary centerline (CL) may be drawn through the tooth 102. With reference to this centerline (CL), each tooth may be moved in orthogonal directions represented by axes 104, 106, and 108 (where 104 is the centerline). The centerline may be rotated about the axis 108 (root angulation) and the axis 104 (torque) as indicated by arrows 110 and 112, respectively. Additionally, the tooth may be rotated about the centerline, as represented by an arrow 114. Thus, all possible free-form motions of the tooth can be performed.

FIG. 2B shows how the magnitude of any tooth movement may be defined in terms of a maximum linear translation of any point P on a tooth 102. Each point PI will undergo a cumulative translation as that tooth is moved in any of the orthogonal or rotational directions defined in FIG. 2A. That is, while the point will usually follow a nonlinear path, there is a linear distance between any point in the tooth when determined at any two times during the treatment. Thus, an arbitrary point PI may in fact undergo a true side-to-side translation as indicated by arrow d1, while a second arbitration point P2 may travel along an arcuate path, resulting in a final translation d2. Many aspects of the present invention are defined in terms of the maximum permissible movement of a point P1 induced on any particular tooth. Such maximum tooth movement, in turn, is defined as the maximum linear translation of that point P1 on the tooth which undergoes the maximum movement for that tooth in any treatment step.

Figure 2C:
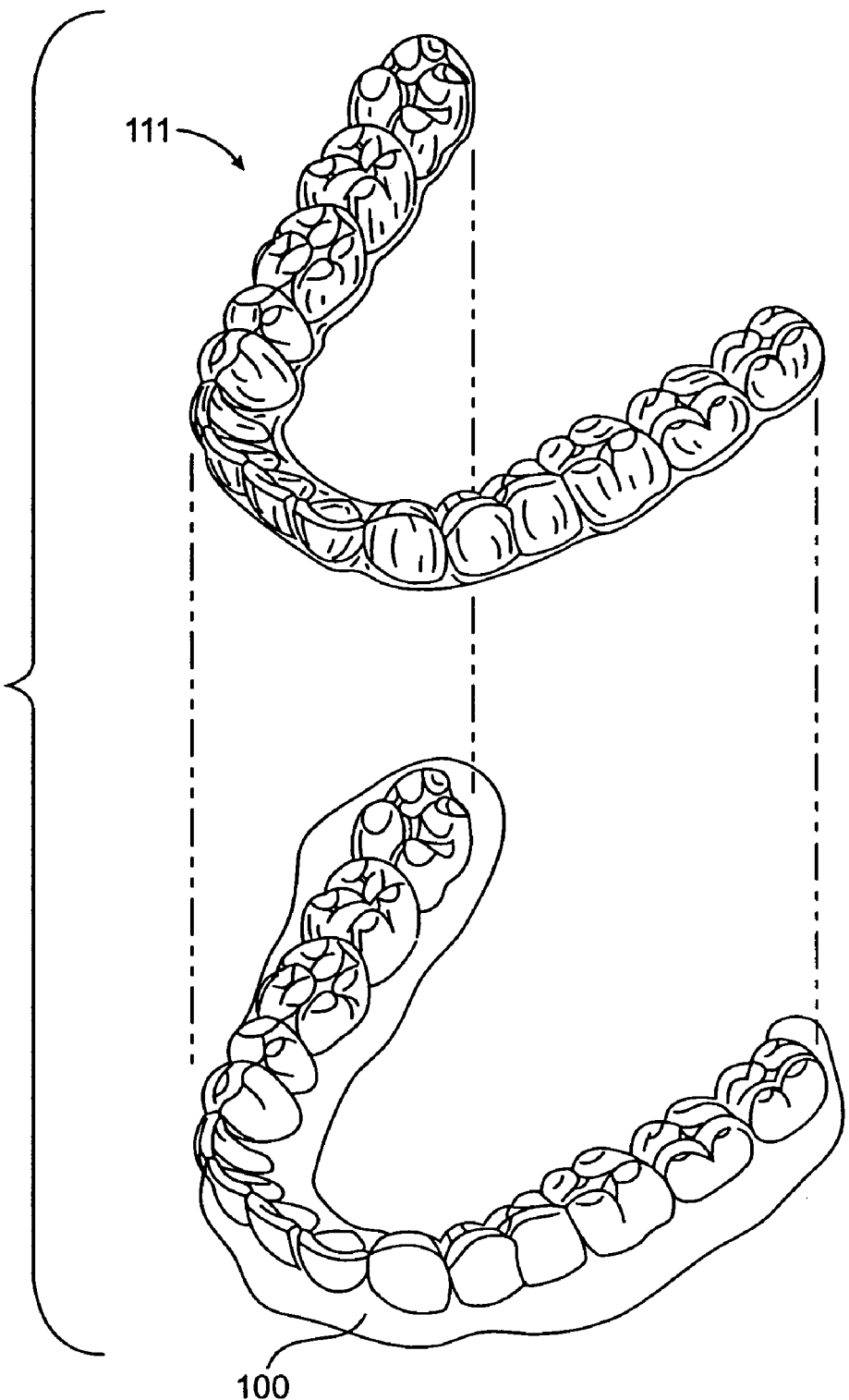
FIG. 2C illustrates the jaw of FIG. 2A together with an incremental position adjustment appliance which has been configured according to the methods and apparatus of the present invention.

FIG. 2C shows one adjustment appliance 111 which is worn by the patient in order to achieve an incremental repositioning of individual teeth in the jaw as described generally above. The appliance is a polymeric shell having a teeth receiving cavity. This is described in U.S. application Ser. No. 09/169,036, filed Oct. 8, 1998, which claims priority from U.S. application Ser. No. 08/947,080, filed Oct. 8, 1997, which in turn claims priority from provisional application No. 06/050,352, filed Jun. 20, 1997 (collectively the "prior applications"), the full disclosures of which are incorporated by reference.

As set forth in the prior applications, each polymeric shell may be configured so that its tooth receiving cavity has a geometry corresponding to an intermediate or final tooth arrangement intended for the appliance. The patient's teeth are repositioned from their initial tooth arrangement to a final tooth arrangement by placing a series of incremental position adjustment appliances over the patient's teeth. The adjustment appliances are generated at the beginning of the treatment, and the patient wears each appliance until the pressure of each appliance on the teeth can no longer be felt. At that point, the patient replaces the current adjustment appliance with the next adjustment appliance in the series until no more appliance remains. Conveniently, the appliances are generally not affixed to the teeth and the patient may place and replace the appliances at any time during the procedure. The final appliance or several appliances in the series may have a geometry or geometries selected to overcorrect the tooth arrangement, i.e., have a geometry which would (if fully achieved) move individual teeth beyond the tooth arrangement which has been selected as the "final." Such overcorrection may be desirable in order to offset potential relapse after the repositioning method has been terminated, i.e., to permit some movement of individual teeth back toward their precorrected positions. Overcorrection may also be beneficial to speed the rate of correction, i.e., by having an appliance with a geometry that is positioned beyond a desired intermediate or final position, the individual teeth will be shifted toward the position at a greater rate. In such cases, the use of an appliance can be terminated before the teeth reach the positions defined by the appliance.

The polymeric shell 111 can fit over all teeth present in the upper or lower jaw. Often, only certain one(s) of the teeth will be repositioned while others of the teeth will provide a base or an anchor region for holding the appliance 111 in place as the appliance 111 applies a resilient repositioning force against the tooth or teeth to be repositioned. In complex cases, however, multiple teeth may be repositioned at some point during the treatment. In such cases, the teeth which are moved can also serve as a base or anchor region for holding the repositioning appliance.

The polymeric appliance 111 of FIG. 2C may be formed from a thin sheet of a suitable elastomeric polymer, such as Tru-Tain 0.03 in, thermal forming dental material, available from Tru-Tain Plastics, Rochester, Minn. Usually, no wires or other means will be provided for holding the appliance in place over the teeth. In some cases, however, it will be desirable or necessary to provide individual anchors on teeth with corresponding receptacles or apertures in the appliance 100 so that the appliance can apply an upward force on the tooth which would not be possible in the absence of such an anchor.

Figure 3:
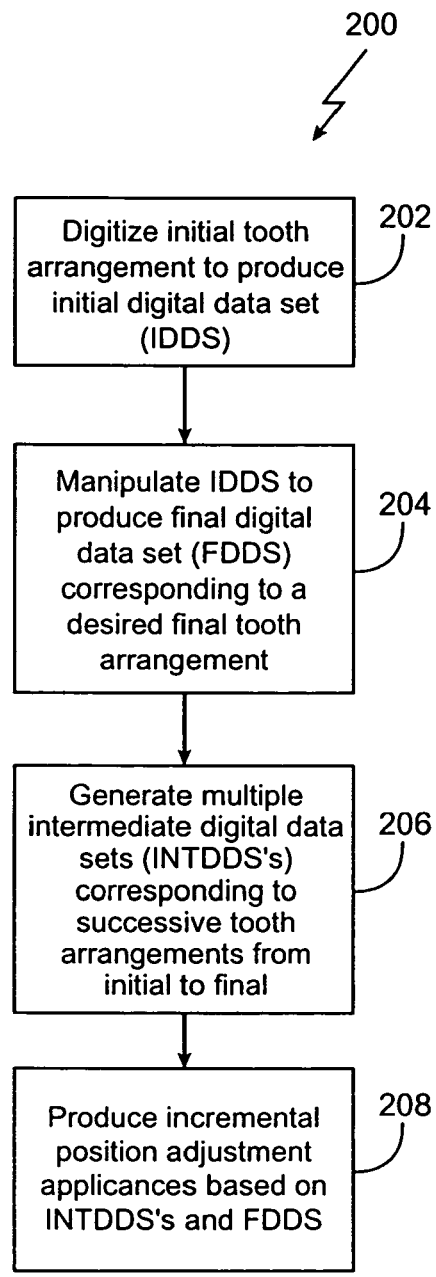
FIG. 3 is a block diagram illustrating a process for producing incremental position adjustment appliances.

FIG. 3 shows a process 200 for producing the incremental position adjustment appliances for subsequent use by a patient to reposition the patient's teeth. As a first step, an initial digital data set (IDDS) representing an initial tooth arrangement is obtained (step 202). The IDDS may be obtained in a variety of ways. For example, the patient's teeth may be scanned or imaged using X-rays, three dimensional X-rays, computer-aided tomographic images or data sets, or magnetic resonance images, among others. The teeth data may be generated by a non destructive scanner, such as the scanner of FIG. 8, or alternatively, can be generated by a destructive scanner, as described in the incorporated-by-reference U.S. Applications.

The IDDS is then manipulated using a computer having a suitable graphical user interface (GUI) and software appropriate for viewing and modifying the images. More specific aspects of this process will be described in detail below.

Individual tooth and other components may be segmented or isolated in the model to permit their individual repositioning or removal from the digital model. After segmenting or isolating the components, the user will often reposition the tooth in the model by following a prescription or other written specification provided by the treating professional. Alternatively, the user may reposition one or more teeth based on a visual appearance or based on rules and algorithms programmed into the computer. Once the user is satisfied, the final teeth arrangement is incorporated into a final digital data set (FDDS) (step 204). The FDDS is used to generate appliances that move the teeth in a specified sequence. First, the centers of each tooth model may be aligned using a number of methods. One method is a standard arch. Then, the teeth models are rotated until their roots are in the proper vertical position. Next, the teeth models are rotated around their vertical axis into the proper orientation. The teeth models are then observed from the side, and translated vertically into their proper vertical position. Finally, the two arches are placed together, and the teeth models moved slightly to ensure that the upper and lower arches properly mesh together. The meshing of the upper and lower arches together is visualized using a collision detection process to highlight the contacting points of the teeth.

Based on both the IDDS and the FDDS, a plurality of intermediate digital data sets (INTDDSs) are defined to correspond to incrementally adjusted appliances (step 206). Finally, a set of incremental position adjustment appliances are produced based on the INTDDs and the FDDS (step 208).

In step 204, final positions for the upper and lower teeth in a masticatory system of a patient are determined by generating a computer representation of the masticatory system. An occlusion of the upper and lower teeth is computed from the computer representation; and a functional occlusion is computed based on interactions in the computer representation of the masticatory system. The occlusion may be determined by generating a set of ideal models of the teeth. Each ideal model in the set of ideal models is an abstract model of idealized teeth placement which is customized to the patient's teeth, as discussed below. After applying the ideal model to the computer representation, and the position of the teeth is optimized to fit the ideal model. The ideal model may be specified by one or more arch forms, or may be specified using various features associated with the teeth.

Figure 4:
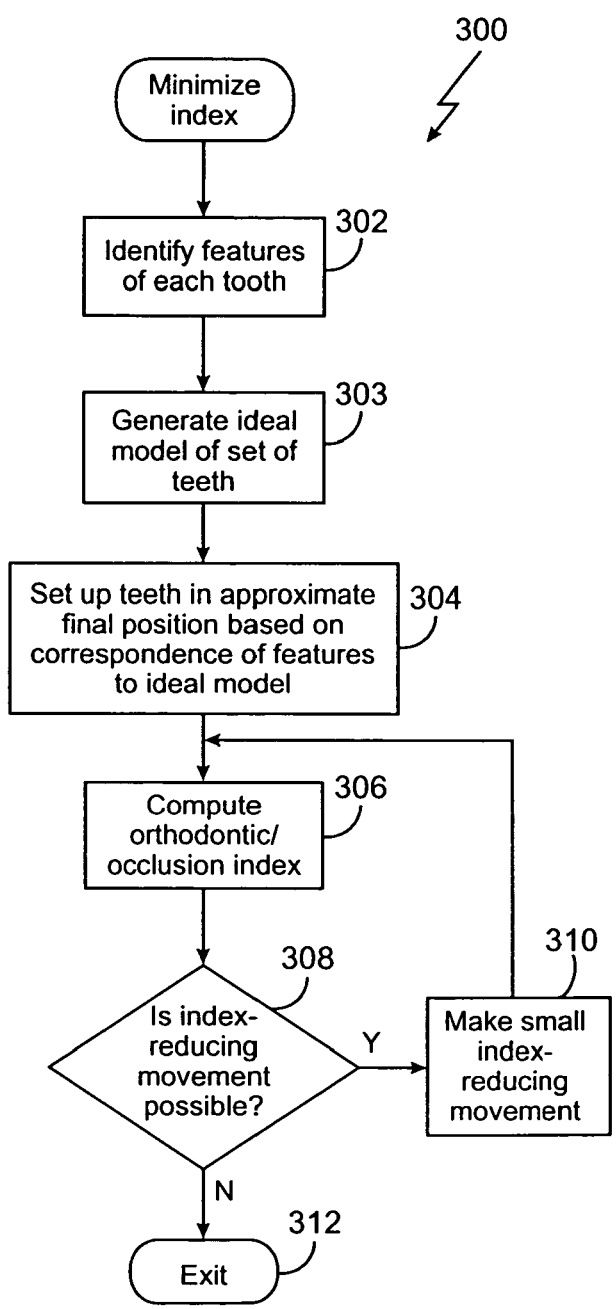
FIG. 4 is a flow chart illustrating a process for optimizing a final placement of the patient's teeth.

FIG. 4 illustrates a process 300 which optimizes the final placement of the teeth based on teeth features. First, the process 300 automatically or, with human assistance, identifies various features associated with each tooth to arrive at a model of the teeth (step 302). An ideal model set of teeth is then generated either from casts of the patient's teeth or from patients with a good occlusion (step 303).

From step 302, the process 300 positions the model of the teeth in its approximate final position based on a correspondence of features to the ideal model (step 304). In that step, each tooth model is moved so that its features are aligned to the features of a corresponding tooth in the ideal model. The features may be based on cusps, fossae, ridges, distance-based metrics, or shape-based metrics. Shape-based metrics may be expressed as a function of the patient's arches, among others.

For example, cusp features associated with each tooth may be used. Cusps are pointed projections on the chewing surface of a tooth. In a detection stage, a possible cusp is viewed as an "island" on the surface of the tooth, with the candidate cusp at the highest point on the island. "Highest" is measured with respect to the coordinate system of the model, but could just as easily be measured with respect to the local coordinate system of each tooth. The set of all possible cusps is determined by looking for all local maxima on the tooth model that are within a specified distance of the top of the bounding box of the model. First, the highest point on the model is designated as the first candidate cusp. A plane is passed through this point, perpendicular to the direction along which the height of a point is measured. The plane is then lowered by a small predetermined distance along the Z axis. Next, all vertices connected to the tooth and which are above the plane and on some connected component are associated with the candidate cusp as cusps. This step is also referred to as a flood fill step. From each candidate cusp point, outward flooding is performed, marking each vertex on the model visited in this matter as part of the corresponding candidate cusp. After the flood fill step is complete, every vertex on the model is examined. Any vertex that is above the plane and has not been visited by one of the flood fills is added to the list of candidate cusps. These steps are repeated until the plane is traveled a specified distance.

After the detection stage, the cusp detection process may include a rejection stage where local geometries around each of cusp candidates are analyzed to determine if they possess non-cusp-like features. Cusp candidates that exhibit non-cusp-like features are removed from the list of cusp candidates. Various criteria may be used to identify non-cusp-like features. According to one test, the local curvature of the surface around the cusp candidate is used to determine whether the candidate possesses non-cusp-like features. Alternatively, a measure of smoothness is computed based on the average normal in an area around the candidate cusp. If the average normal deviates from the normal at the cusp by more than a specified amount, the candidate cusp is rejected.

Next, the process 300 computes an orthodontic/occlusion index (step 306). One index which may be used is the PAR (Peer Assessment Rating) index. In addition to PAR, other metrics such as shape-based metrics or distance-based metrics may be used.

The PAR index identifies how far a tooth is from a good occlusion. A score is assigned to various occlusal traits which make up a malocclusion. The individual scores are summed to obtain an overall total, representing the degree a case deviates from normal alignment and occlusion. Normal occlusion and alignment is defined as all anatomical contact points being adjacent, with a good intercuspal mesh between upper and lower buccal teeth, and with nonexcessive overjet and overbite.

In PAR, a score of zero would indicate good alignment, and higher scores would indicate increased levels of irregularity. The overall score is recorded on pre- and posttreatment dental casts. The difference between these scores represents the degree of improvement as a result of orthodontic intervention and active treatment. The eleven components of the PAR Index are: upper right segment; upper anterior segment; upper left segment; lower right segment; lower anterior segment; lower left segment; right buccal occlusion; overjet; overbite; centerline; and left buccal occlusion. In addition to the PAR index, other indices may be based on distances of the features on the tooth from their ideal positions or ideal shapes.

From step 306, the process 300 determines whether additional index-reducing movements are possible (step 308). Here, all possible movements are attempted, including small movements along each major axis as well as small movements with minor rotations. An index value is computed after each small movement and the movement with the best result is selected. In this context, the best result is the result that minimizes one or more metrics such as PAR-based metrics, shape-based metrics or distance-based metrics. The optimization may use a number of techniques, including simulated annealing technique, hill climbing technique, best-first technique, Powell method, and heuristics technique, among others. Simulated annealing techniques may be used where the index is temporarily increased so that another path in the search space with a lower minimum may be found. However, by starting with the teeth in an almost ideal position, any decrease in the index should converge to the best result.

In step 308, if the index can be optimized by moving the tooth, incremental index-reducing movement inputs are added (step 310) and the process loops back to step 306 to continue computing the orthodontic/occlusion index. Alternatively, in the event that the index cannot be optimized any more, the process 300 exits (step 312).

Turning now to FIG. 5, a process 320 for performing functional occlusion is shown. Functional occlusion is a process for determining how well the teeth fit together when the jaws move. The process 320 first acquires tooth/arch jaw registration. This may be done using conventional techniques such as X-ray, a computer tomography, or a mechanical device such as a face bow transfer.

After acquiring the registration information, the process 320 places digital dental models of the teeth in a digital articulation simulator (step 324). The articulation simulator allows a subset of jaw movements such as bite-movements to be simulated, as described below.

From step 324, the process 320 simulates jaw motions (step 326). A simplified set of movement physics (kinematics) is applied to the dental models. The process 320 performs a simulation using a simplified set of interacting forces on the jaws 100 and 101 in relation to one another. The simplified physical simulation allows the system to focus on motions involving much contact between the jaws. The physical simulation allows the system to render realistic physically correct jaw movements when the jaws 100 and 101 come into contact with each other.

A range of simulated motion may be supplied using a library of motions. One typical motion supplied by the library is a protrusive motion where the lower jaw 101 is moved forward and backward to bring the front teeth on both jaws into contact with each other. Another motion is a lateral motion found in food chewing. The lateral motion involves moving the jaws 100 and 101 side to side. Other motions that may be supplied in the library include motions that are "tooth guided" where the path of the lower jaw 100 is guided by the teeth in contact with each other.

Next, the process 320 adjusts the final position based on contacts observed during the simulation of motions in step 326 (step 328). The result of the simulation is analyzed, the position of each tooth can be adjusted if contacts associated with that tooth are deemed excessive.

Finally, based on the contact data generated, the process determines whether additional motion simulations need to be done. The motion simulation may be rerun until the contacts associated with each tooth are acceptable to the treating orthodontist. The tooth model manipulation process can be done subjectively, i.e., the user may simply reposition teeth in an aesthetically and/or therapeutically desired manner based on observations of the final position or based on the simulation of contacts. Alternatively, rules and algorithms may be used to assist the user in repositioning the teeth based on the contacts. If the simulation needs to be repeated, the process loops back to step 326 (step 330). Alternatively, the process exits (step 332).

FIG. 6 shows an optional process of 340 of incorporating midtreatment information to the final positioning process. First, a digital model incorporating dental information associated with the patient is generated from a scan of the patient's teeth (step 342). The scan may be performed using casts, X-rays or any of the conventional scanning methods.

Next, the digital model is segmented into one model for each tooth (step 344). Each tooth is then matched against a model associated with a prior scan developed at the beginning of the treatment plan (step 346). The matching process is based on matching corresponding points between the current scan and the prior scan of the teeth. In most cases, the teeth segmented from the current scan retain the shapes determined at the beginning of the treatment plan, and the matching process is easy because the models should be similar to each other.

A final position transform is then applied to the new teeth model (step 348). The final position and specification from the prior model is copied to the current model of the patient, and the final position is adjusted based on the new models, the new X-ray information or a new prescription (step 350). Step 350 basically involves rerunning the minimization process 300 (FIG. 4) described previously with the new information, which may be a slight change in the model, a change in the X-ray scan, or a change the prescription. Finally, the process 340 exits (step 352).

Figure 7:
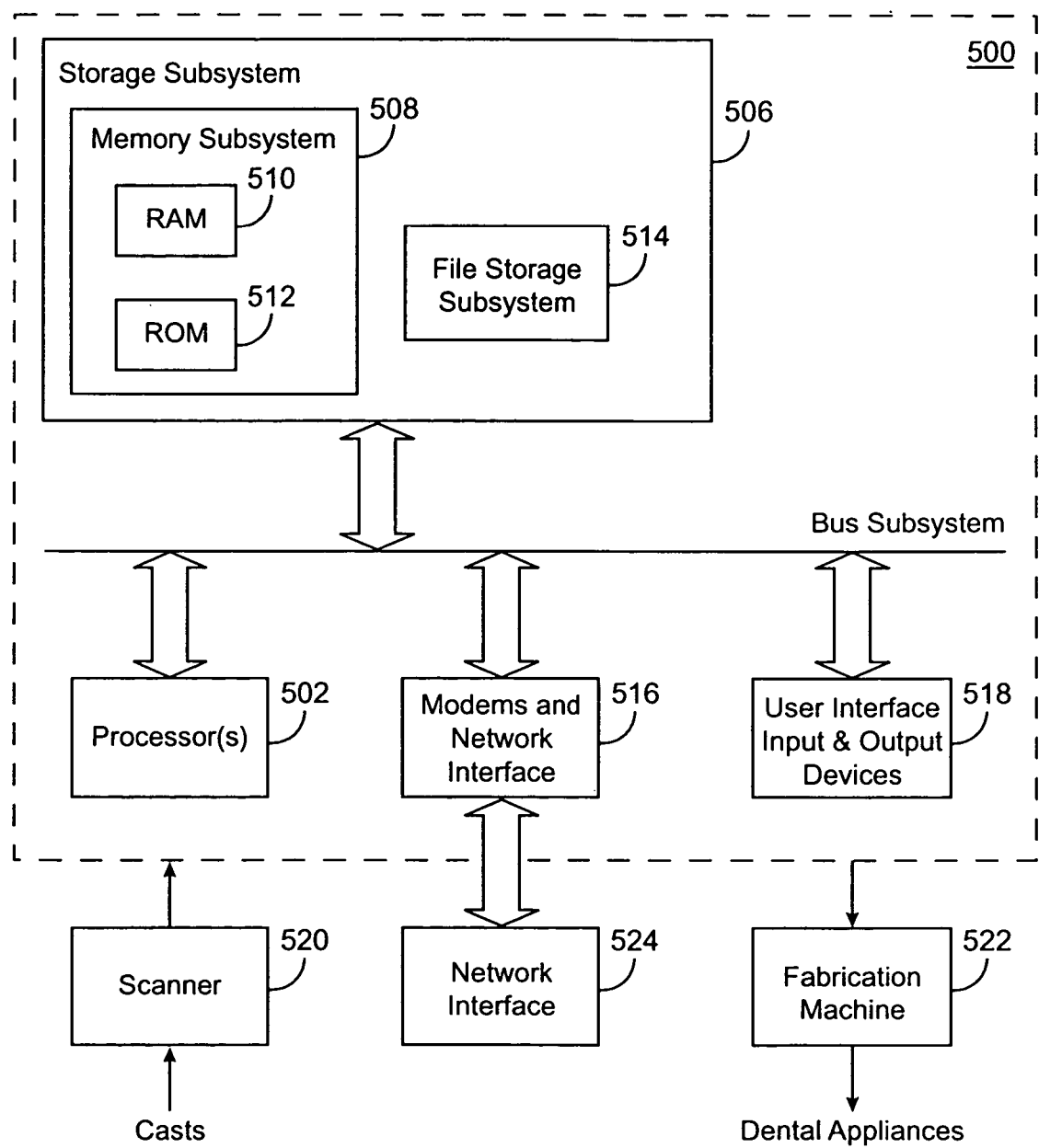
FIG. 7 is a block diagram illustrating a system for generating appliances in accordance with the present invention.

FIG. 7 is a simplified block diagram of a data processing system 500. Data processing system 500 typically includes at least one processor 502 which communicates with a number of peripheral devices over bus subsystem 504. These peripheral devices typically include a storage subsystem 506 (memory subsystem 508 and file storage subsystem 514), a set of user interface input and output devices 518, and an interface to outside networks 516, including the public switched telephone network. This interface is shown schematically as "Modems and Network Interface" block 516, and is coupled to corresponding interface devices in other data processing systems over communication network interface 524. Data processing system 500 may include a terminal or a low-end personal computer or a high-end personal computer, workstation or mainframe.

The user interface input devices typically include a keyboard and may further include a pointing device and a scanner. The pointing device may be an indirect pointing device such as a mouse, trackball, touchpad, or graphics tablet, or a direct pointing device such as a touchscreen incorporated into the display. Other types of user interface input devices, such as voice recognition systems, may be used.

User interface output devices may include a printer and a display subsystem, which includes a display controller and a display device coupled to the controller. The display device may be a cathode ray tube (CRT), a flat-panel device such as a liquid crystal display (LCD), or a projection device. The display subsystem may also provide nonvisual display such as audio output.

Storage subsystem 506 maintains the basic programming and data constructs that provide the functionality of the present invention. The software modules discussed above are typically stored in storage subsystem 506. Storage subsystem 506 typically comprises memory subsystem 508 and file storage subsystem 514.

Memory subsystem 508 typically includes a number of memories including a main random access memory (RAM) 510 for storage of instructions and data during program execution and a read only memory (ROM) 512 in which fixed instructions are stored. In the case of Macintosh-compatible personal computers the ROM would include portions of the operating system; in the case of IBM-compatible personal computers, this would include the BIOS (basic input/output system).

File storage subsystem 514 provides persistent (nonvolatile) storage for program and data files, and typically includes at least one hard disk drive and at least one floppy disk drive (with associated removable media). There may also be other devices such as a CD-ROM drive and optical drives (all with their associated removable media). Additionally, the system may include drives of the type with removable media cartridges. The removable media cartridges may, for example be hard disk cartridges, such as those marketed by Syquest and others, and flexible disk cartridges, such as those marketed by Iomega. One or more of the drives may be located at a remote location, such as in a server on a local area network or at a site on the Internet's World Wide Web.

In this context, the term "bus subsystem" is used generically so as to include any mechanism for letting the various components and subsystems communicate with each other as intended. With the exception of the input devices and the display, the other components need not be at the same physical location. Thus, for example, portions of the file storage system could be connected over various local-area or wide-area network media, including telephone lines. Similarly, the input devices and display need not be at the same location as the processor, although it is anticipated that the present invention will most often be implemented in the context of PCS and workstations.

Bus subsystem 504 is shown schematically as a single bus, but a typical system has a number of buses such as a local bus and one or more expansion buses (e.g., ADB, SCSI, ISA, EISA, MCA, NuBus, or PCI), as well as serial and parallel ports. Network connections are usually established through a device such as a network adapter on one of these expansion buses or a modem on a serial port. The client computer may be a desktop system or a portable system.

Scanner 520 is responsible for scanning casts of the patient's teeth obtained either from the patient or from an orthodontist and providing the scanned digital data set information to data processing system 500 for further processing. In a distributed environment, scanner 520 may be located at a remote location and communicate scanned digital data set information to data processing system 500 over network interface 524.

Fabrication machine 522 fabricates dental appliances based on intermediate and final data set information received from data processing system 500. In a distributed environment, fabrication machine 522 may be located at a remote location and receive data set information from data processing system 500 over network interface 524.

Figure 8:
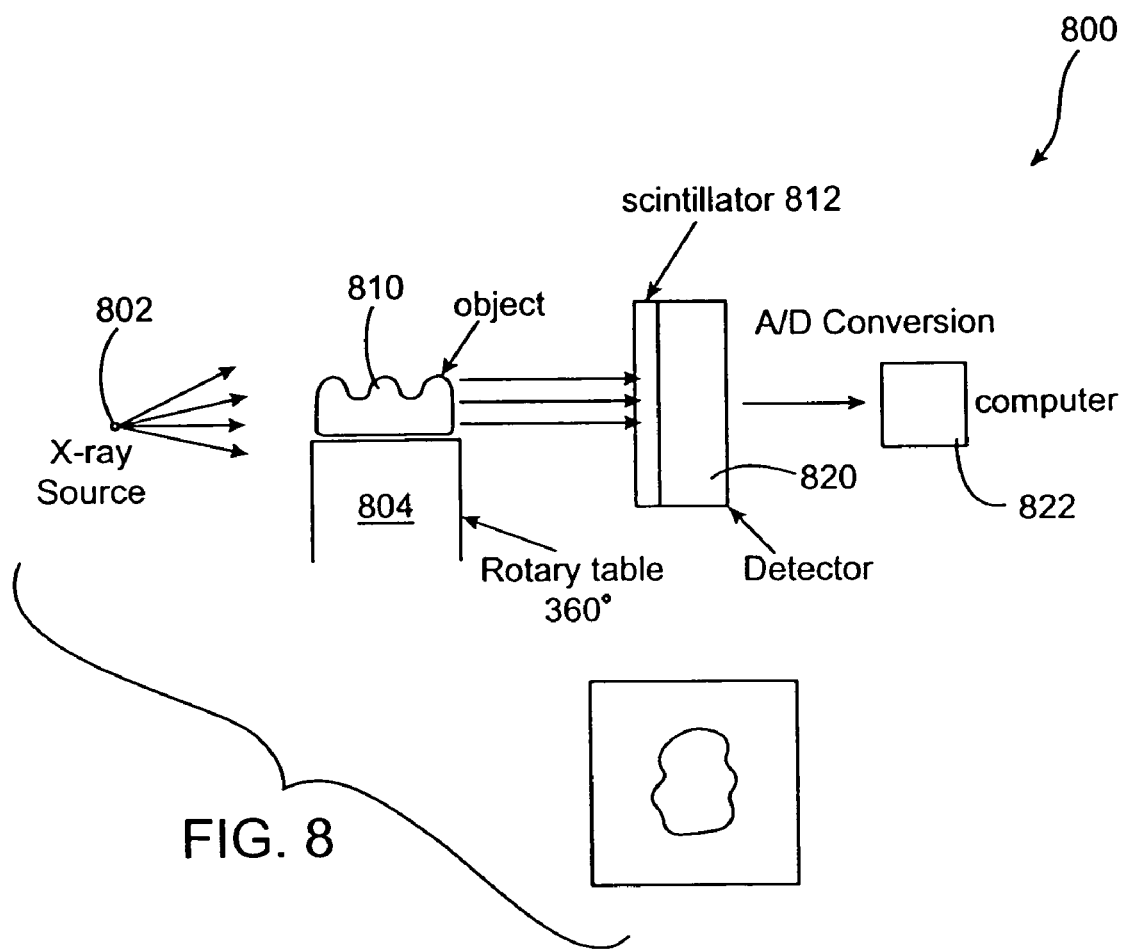
FIG. 8 is a block diagram of one scanner embodiment.

FIG. 8 shows one embodiment of the scanner 520 of FIG. 7. A scanner 800 is an X-ray scanner. The scanner 800 has a rotating table 804 including a table top that has sufficient space for one or two impressions 810 to rest on it. The impression 810 can be irradiated by a flat fan-shaped X-ray beam 803 emitted by an X-ray source 802. The radiation is swept by the impression 810 and passes through a scintillator 812. Radiation transmitted by the scintillator 812 is measured by an X-ray detector 820. The detector 820 performs an analog to digital conversion and provides this information to a computer 822. The computer 822 captures on cross sectional scan and instructs the rotating table 804 to rotate to its next position and another scan is performed until the entire impression 810 is scanned. The X-ray source 802, the scintillator 812, the detector 820 and the rotatable table 804 thus obtains an image of a cross-section of (a part of) the impression 810 by computer tomography (CT). The CT system scans impressions of patients' teeth and eliminates the need to create a plaster model for each jaw. Software on the computer 822 automatically extracts a positive model out of the scan data. The upper and lower jaw will then be put together using the information from the scan data of a wax bite. In one embodiment, the scanner 800 utilizes a technique called "cone beam reconstruction."

Figure 9:
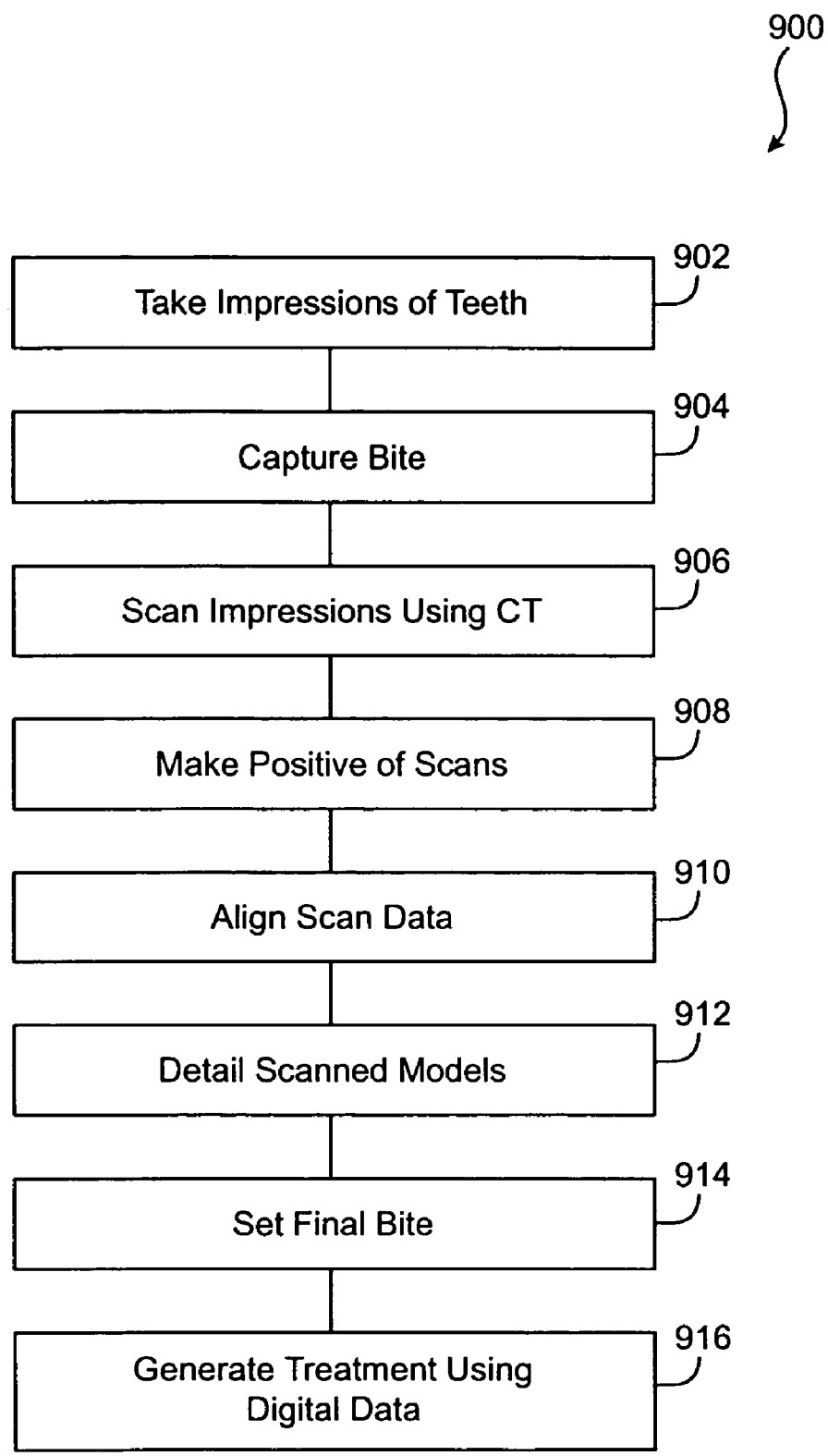
FIG. 9 is a flowchart illustrating an exemplary process for treating a patient using the scanner of FIG. 8.

FIG. 9 shows one process 900 for digitally scanning and generating a model of the patient's teeth for treatment. The process 900 is as follows:

1. Impression of a patient is taken in a plastic tray (902).
2. A bite of the patient will be taken. A suitable material for capturing the bite is PVS material in order to capture detailed tooth geometry. Wax bites may also be used but results can be worse based on definition on the bite (904).
3. The upper, lower and the bite will be scanned together in the CT machine (906).
4. Once scanned, the upper and lower impression scanned data is digitally reversed to make a positive. This is done by identifying the inner most surface of the impression material and extracting it from the rest of the data using a largest connected component algorithm (908).
5. Once the upper and lower data is obtained, they will be aligned into a bite position using the bite material scanned (910).
6. The models are digitally detailed. Any excess material or defects in the material will have to be cleaned up (process is known as detailing) (912).
7. Once the models are cleaned, the final bite needs to be set. Models are articulated by an operator till the relative position closely resembles that of the actual mouth (914).
8. The model is now ready for treatment. The teeth are already cut as part of the detailing operation (916).

Various alternatives, modifications, and equivalents may be used in lieu of the above components. Although the final position of the teeth may be determined using computer-aided techniques, a user may move the teeth into their final positions by independently manipulating one or more teeth while satisfying the constraints of the prescription.

Additionally, the techniques described here may be implemented in hardware or software, or a combination of the two. The techniques may be implemented in computer programs executing on programmable computers that each includes a processor, a storage medium readable by the processor (including volatile and nonvolatile memory and/or storage elements), and suitable input and output devices. Program code is applied to data entered using an input device to perform the functions described and to generate output information. The output information is applied to one or more output devices.

Each program can be implemented in a high level procedural or object-oriented programming language to operate in conjunction with a computer system. However, the programs can be implemented in assembly or machine language, if desired. In any case, the language may be a compiled or interpreted language.

Each such computer program can be stored on a storage medium or device (e.g., CD-ROM, hard disk or magnetic diskette) that is readable by a general or special purpose programmable computer for configuring and operating the computer when the storage medium or device is read by the computer to perform the procedures described. The system also may be implemented as a computer-readable storage medium, configured with a computer program, where the storage medium so configured causes a computer to operate in a specific and predefined manner.

Further, while the invention has been shown and described with reference to an embodiment thereof, those skilled in the art will understand that the above and other changes in form and detail may be made without departing from the spirit and scope of the following claims.

What is claimed is:

1. A method to create a digital model of a patient's teeth, comprising:
   creating an impression of the patient's teeth;
   scanning the impression using an X-ray source as to generate scan data comprising an image of at least a portion of the impression; and
   generating a positive digital model of the patient's teeth with the X-ray scan data, the generating comprising digitally reversing the X-ray scan data to make positive data.

2. The method of claim 1, further comprising using passing the radiation source through a scintillator.

3. The method of claim 2, further comprising digitizing the output of the scintillator.

4. The method of claim 1, wherein the impression of the teeth is taken in a plastic tray.

5. The method of claim 1, further comprising taking a bite impression of the patient.

6. The method of claim 5, wherein the bite impression is taken using a PVS material.

7. The method of claim 5, wherein the bite impression is taken using a wax bite.

8. The method of claim 1, wherein an upper teeth impression, a lower teeth impression and a bite impression is scanned together.

9. The method of claim 8, further comprising digitally reversing data from the upper and lower impression scan data to make positive data.

10. The method of claim 9, wherein the digital reversing identifies inner surfaces of an impression material and extracting the inner surfaces using a largest connected component algorithm.

11. The method of claim 1, further comprising aligning data into a bite position using the bite material scanned.

12. The method of claim 1, further comprising digitally detailing the teeth data.

13. The method of claim 1, further comprising setting a final bite.

14. The method of claim 1, further comprising articulating the digital model.

15. The method of claim 1, further comprising treating a patient using the digital model.

16. The method of claim 1, further comprising:
generating a computer representation of a masticatory system of the patient; and
determining an occlusion from the computer representation of the masticatory system.

17. The method of claim 16, wherein the occlusion is a static occlusion, further comprising:
modeling an ideal set of teeth;
automatically applying the ideal set of teeth to the computer representation of a masticatory system of the patient; and
optimizing the position of the patient's teeth to fit the ideal set of teeth.

18. The method of claim 17, wherein the modeling step further comprises selecting one or more arch forms specifying the ideal set of teeth.

19. The method of claim 17, wherein the masticatory system includes jaws and wherein the applying step includes:
registering a model of the upper and lower teeth with a model of the masticatory system;
simulating the motion of the jaws to generate contact data between the upper and lower teeth; and
placing a tooth in a final position based on the contact data.

20. The method of claim 19, wherein the model is registered using X-ray data.

21. The method of claim 19, wherein the model is registered using computed tomography data.

22. The method of claim 19, wherein the model is registered using data associated with a mechanical model.

23. The method of claim 19, wherein the simulating step further comprises applying kinematics to the model of the teeth.

24. The method of claim 19, wherein the simulating step further comprises applying a constrained motion to the model of the tooth.

25. The method of claim 19, wherein the placing step is based on a measure of undesirability to the contacts.

26. The method of claim 25, further comprising optimizing the position of the tooth according to the measure of undesirability.

27. The method of claim 26, further comprising minimizing the measure of undesirability.

28. The method of claim 27, wherein the measure of undesirability is a function of one or more of Peer Assessment Rating (PAR) metrics, distance-based metrics and shape-based metrics.

29. The method of claim 17, wherein the simulating step includes providing a library of motions.

30. The method of claim 29, wherein the library of motions includes a protrusive motion.

31. The method of claim 29, wherein the library of motions includes a lateral motion.

32. The method of claim 29, wherein the library of motions includes tooth-guided motions.

33. The method of claim 17, wherein the simulating step includes applying physical forces to one jaw.

34. The method of claim 17, wherein the placing step further includes updating the computer representation of the masticatory system with new patient data.

35. The method of claim 34, wherein the patient has a first teeth model, further comprising:
scanning the teeth of the patient to generate a second teeth model;
matching the second teeth model with the first teeth model;
applying a final position transform to the second teeth model; and
adjusting the position of teeth in the second model based on new information.

36. An apparatus to create a digital model of a patient's teeth, comprising:
a an X-ray radiation source;
a scintillator to receive the radiation from the X-ray radiation source;
a radiation detector coupled to the scintillator;
a rotatable table positioned between the X-ray radiation source and the scintillator, the table being adapted to support an impression of the patient's teeth; and
a computer coupled to the detector, the computer comprising a computer-readable medium having instructions that, if executed by the computer, will cause the apparatus to:
scan the impression using the X-ray radiation source as to generate scan data comprising an image of at least a portion of the impression; and
generate a positive digital model of the patient's teeth with the X-ray scan data, the generating comprising digitally reversing the X-ray scan data to make positive data.

37. The apparatus of claim 36, wherein the radiation source is a computed tomography source.

38. The apparatus of claim 36, wherein the rotatable table is adapted to support an upper teeth impression, a lower teeth impression and a bite impression.

39. The apparatus of claim 36, further comprising a fabrication machine coupled to the computer to generate a plurality of appliances, wherein the appliances comprise polymeric shells having cavities and wherein the cavities of successive shells have different geometries shaped to receive and resiliently reposition the teeth from one arrangement to a successive arrangement.

* * * * *